United States Patent
Lee et al.

(10) Patent No.: US 7,300,523 B2
(45) Date of Patent: Nov. 27, 2007

(54) METHOD FOR SELECTIVELY WASHING USED REACTION CUVETTES IN AN AUTOMATIC ANALYZER

(75) Inventors: Ching-Cherng Lee, Newark, DE (US); Donald Richard Phillips, Sr., Newark, DE (US); Arnold Lloyd Lewis, Bear, DE (US); William Jackson Devlin, Sr., Lincoln University, PA (US)

(73) Assignee: Dade Behring Inc., Deerfield, IL (US)

( * ) Notice: Subject to any disclaimer, the term of this patent is extended or adjusted under 35 U.S.C. 154(b) by 86 days.

(21) Appl. No.: 10/623,360

(22) Filed: Jul. 18, 2003

(65) Prior Publication Data
US 2005/0014274 A1  Jan. 20, 2005

(51) Int. Cl.
*G01N 35/02* (2006.01)
*B08B 3/04* (2006.01)
*B08B 5/04* (2006.01)
*B08B 9/093* (2006.01)

(52) U.S. Cl. .................. 134/18; 134/10; 134/22.1; 134/21; 134/26; 422/64; 422/67; 436/49

(58) Field of Classification Search ............ 134/18, 134/22.1, 22.11–22.19, 78–80, 95.2, 102.3, 134/10, 26, 30, 21; 422/64, 67; 436/49
See application file for complete search history.

(56) References Cited

U.S. PATENT DOCUMENTS

| | | | | |
|---|---|---|---|---|
| 4,325,910 A | * | 4/1982 | Jordan | 422/64 |
| 4,785,407 A | * | 11/1988 | Sakagami | 702/22 |
| 5,380,487 A | * | 1/1995 | Choperena et al. | 422/63 |
| 5,679,309 A | * | 10/1997 | Bell | 422/67 |
| 5,730,938 A | | 3/1998 | Carbonari et al. | |
| 5,741,461 A | | 4/1998 | Takahashi et al. | |
| 6,027,691 A | | 2/2000 | Watts et al. | |
| 6,197,255 B1 | | 3/2001 | Miyake et al. | |
| 6,403,379 B1 | | 6/2002 | Munson et al. | |
| 6,422,248 B1 | | 7/2002 | Fürst et al. | |
| 6,575,181 B1 | | 6/2003 | Wimmer | |
| 2004/0115095 A1 | * | 6/2004 | Devlin et al. | 422/63 |

* cited by examiner

*Primary Examiner*—Zeinab El-Arini
(74) *Attorney, Agent, or Firm*—Leland K. Jordan

(57) ABSTRACT

A method for cleansing used reaction cuvettes so that whenever certain assays are to be or have been performed in the reaction cuvette, the cuvette is automatically subjected to an additional cleaning operation by providing a number of washing and drying manifolds, each of which is independently selectively activated to perform or not perform a cleaning operation.

5 Claims, 17 Drawing Sheets

METHOD FOR SELECTIVELY WASHING USED REACTION CUVETTES IN AN AUTOMATIC ANALYZER

FIELD OF THE INVENTION

The present invention relates to a method and apparatus for automatically processing a patient's biological fluids such as urine, blood serum, plasma, cerebrospinal fluid and the like. In particular, the present invention provides alternate methods to wash a used reaction cuvette in a analyzing system by considering the identity of an assay to be next performed therein.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain end-point or rate values from which an amount of analyte may be determined using well-known calibration techniques.

Although various known clinical analyzers for chemical, immunochemical and biological testing of samples are available, analytical clinical technology is challenged by increasing needs for improved levels of analysis. Due to increasing pressures on clinical laboratories to reduce cost-per-reportable result, there continues to be a need for improvements in the overall cost performance of automated clinical analyzers. In particular, sample analysis continuously needs to be more cost effective in terms of reducing consumables or the cost thereof required for each and every reaction assay.

One contributor to reducing cost-per-reportable result is the ability to repeatedly perform reaction assays in reaction cuvettes that are washed or otherwise cleaned after a first reaction is completed and between subsequent reaction assays. What has been overlooked, however, in many such cleaning systems, is that washing techniques are not fully capable of restoring a cleaned used cuvette to the degree of cleanliness of an unused cuvette. Thus, reagent residues from a prior reaction assay may remain in a washed reaction cuvette. Certain highly sensitive assays may be caused to have inaccurate results if certain reagent residues from preceding reaction assays are present in a cleansed reaction cuvette. One solution is to simply use a new reaction cuvette for each new assay however this defeats the desire to obtain a lower cost-per-reportable result by advantageously washing and reusing reaction cuvettes.

U.S. Pat. No. 5,741,461 discloses a sample analysis system having means for judging in advance of sample addition whether any of a plurality of reaction cuvettes located between a cleaning position and the sample addition position should be cleaned when the analyzer starts to operate.

U.S. Pat. No. 5,679,309 discloses an automatic analyzing apparatus having first and second wash complement cuvettes positioned at a wash point when reactant is added at first and second reactant addition points to the target cuvette. Once the wash complements are determined, the analyzer compares the complements with the inventory of wash designated cuvettes. If the first wash complement is designated for wash, the controller indexes and parks the reaction carousel for reactant addition at the first addition point to the targeted cuvette while simultaneously and opportunistically washing of the first wash complement cuvette. If the first wash complement cuvette is not ready to be washed but the second wash complement cuvette is, the analyzer indexes and parks the reaction carousel for addition of reactant to the targeted cuvette at the second reactant addition point and simultaneously and opportunistically washing of the second wash complement cuvette. If neither of the first or second wash complement cuvettes are ready for wash, no washing occurs and the analyzer indexes and parks the targeted cuvette at the first reaction addition point and reactant is added.

U.S. Pat. No. 6,027,691 discloses a cuvette wash station probe supply and disposal assembly for alternatively (1) providing pressurized washing liquid from a source of washing liquid to the cuvette wash station probe for washing a cuvette disposed within the random access analyzing station at the cuvette washing site and (2) providing a negative pressure to the internal chamber of the cuvette wash station probe for removing waste liquids from a cuvette disposed within the random access analyzing station at the analyzing site and for transferring such waste liquids to a disposal site.

From this discussion of the art state in automated clinical analyzers, it may be seen that while has been considerable progress has been made toward increasing assay processing efficiency, there remains an unmet need for a method for cleansing and reusing a reaction cuvette in an analyzer without sacrificing assay quality. In particular, the present invention presents a method to operate a multi-stall wash station so as to selectively wash a cuvette if the assay next performed in the cuvette is determined to be a highly sensitive or "exceptional" assay.

SUMMARY OF THE INVENTION

The principal object of the invention is to provide an automated wash station adapted for cleansing a used reaction cuvette in an automated analyzer so that whenever certain "exceptional" assays are scheduled to be next performed in a reaction cuvette, the used reaction cuvette is automatically subjected to an additional cleansing or cleaning operation, the terms "cleaning and cleansing" including washing, rinsing, and drying. This objective of selective cleaning of a used reaction cuvette is partially achieved by providing a number of washing and drying manifolds, each of which is independently selectively activated to perform or not perform a cleaning operation, depending upon the identity of the assay scheduled to be next performed in that reaction cuvette. Further, the wash station is operated so that biohazard waste residues from biochemical reactions in a cuvette are segregated from chemical waste residues from chemical reactions in a cuvette. Another feature of the wash station is a "break away" magnetic clamp adapted to ensure full penetration of a drying boot into a cuvette but to automatically break-away whenever a cuvette is not scheduled to be dried and the drying boot is not to be inserted into a cuvette. Hereinafter, a washed used cuvette may be identified as a "cleaned cuvette" and the term "new cuvette" means a cuvette in which no assay has previously been conducted. The analyzer typically includes a circular rotatable assay reaction carousel for holding assay reaction cuvettes and providing stepwise movements in a circular direction, the stepwise movements being separated by stationary dwell times, during which dwell time the wash station may conduct washing and drying operations so as to clean reaction cuvettes. An analyzer like those on which the present wash station may be used advantageously typically has a plurality of conventional assay operation stations at which are positioned individual assay devices, such as sensors, reagent add stations, mixing stations, separation stations, measuring stations and the like.

DETAILED DESCRIPTION OF THE INVENTION

Figure 1:
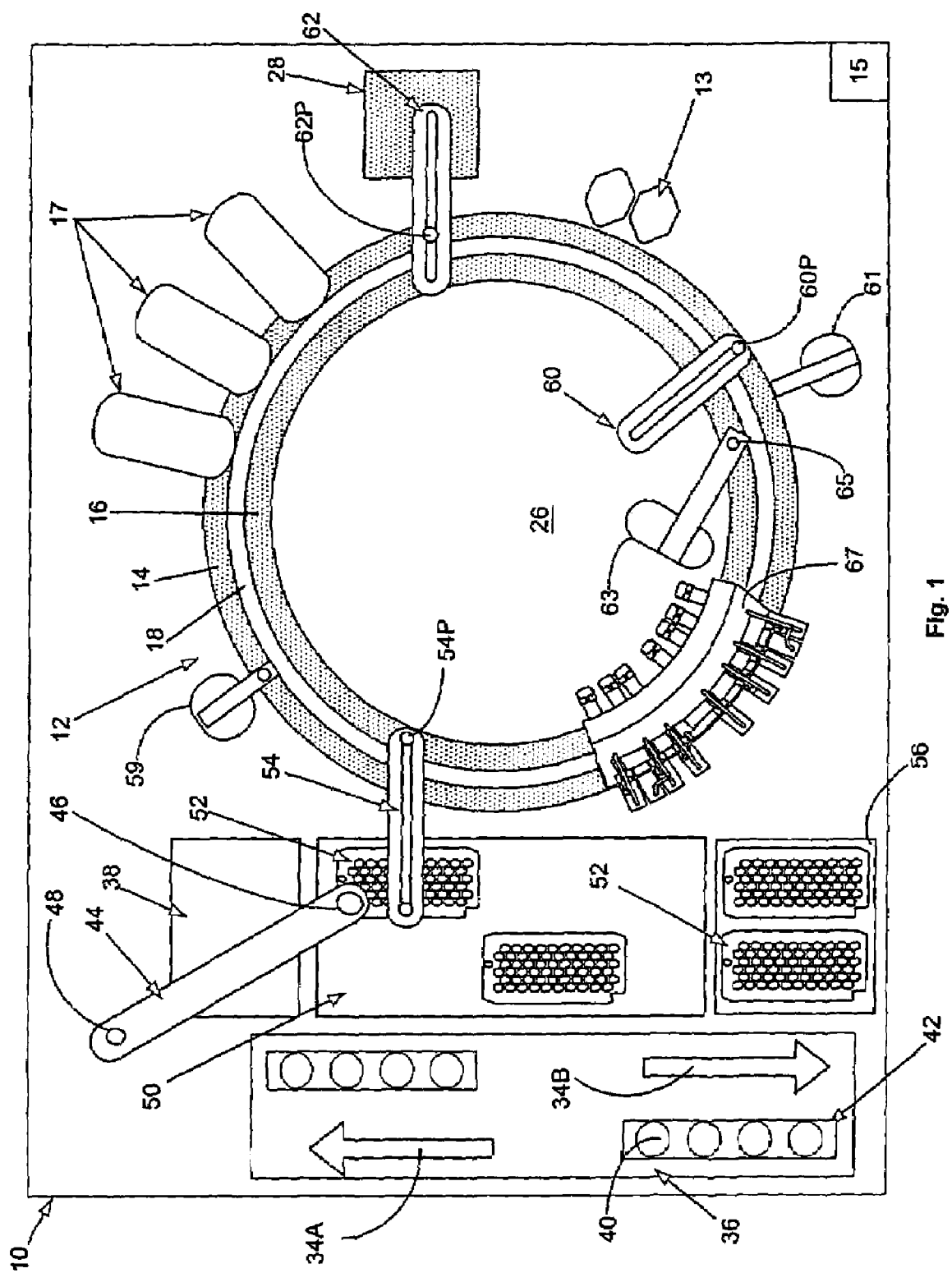
FIG. 1 is a schematic plan view of an automated analyzer in which the present invention may be employed to advantage.
Figure 2:
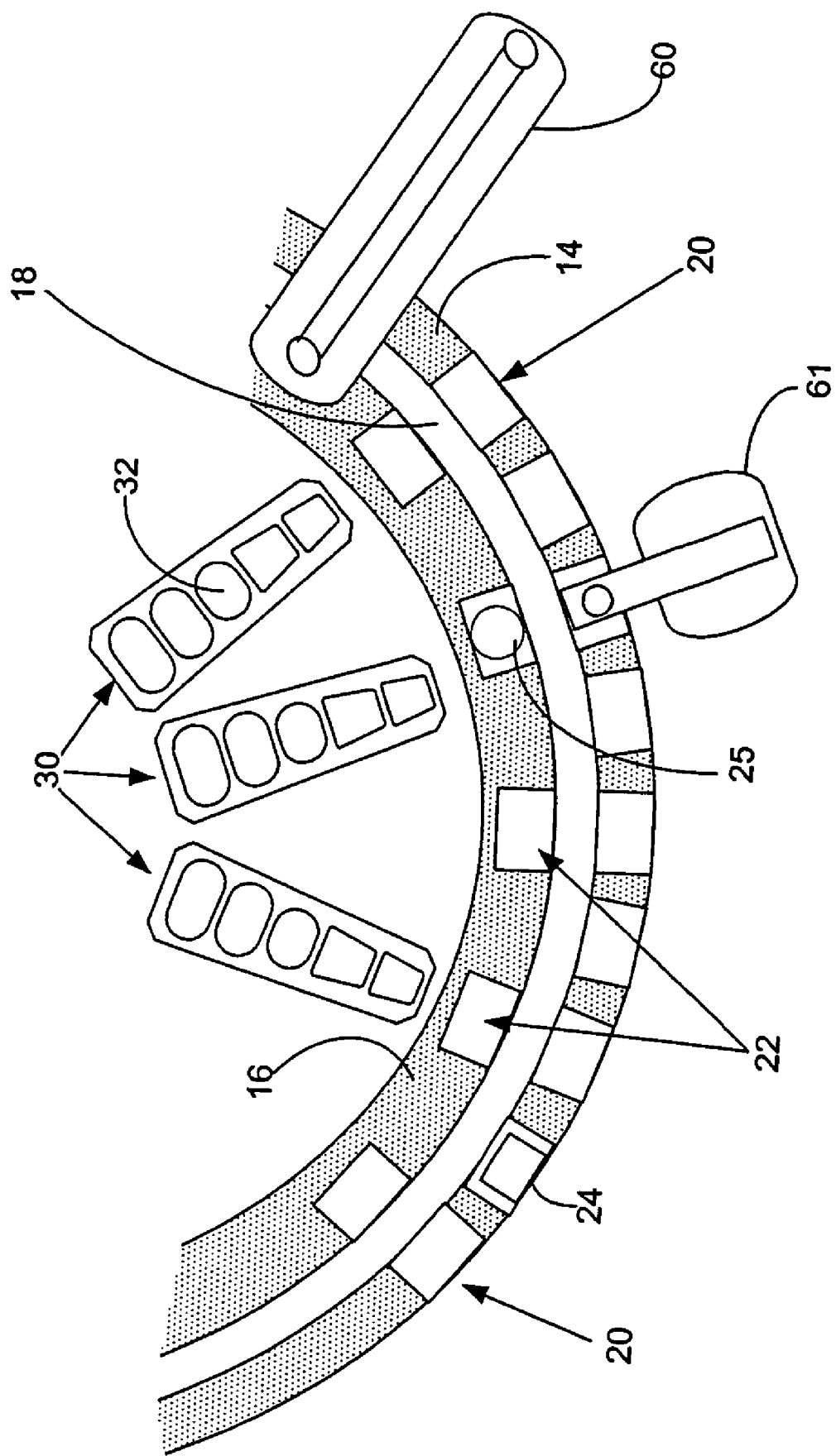
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

Temperature-controlled reagent storage areas 26 and 28 store a plurality of multi-compartment elongate reagent cartridges 30 like that described in co-pending application Ser. No. 09/949,132 assigned to the assignee of the present invention, and containing reagents in wells 32 as necessary to perform a given assay.

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 3:
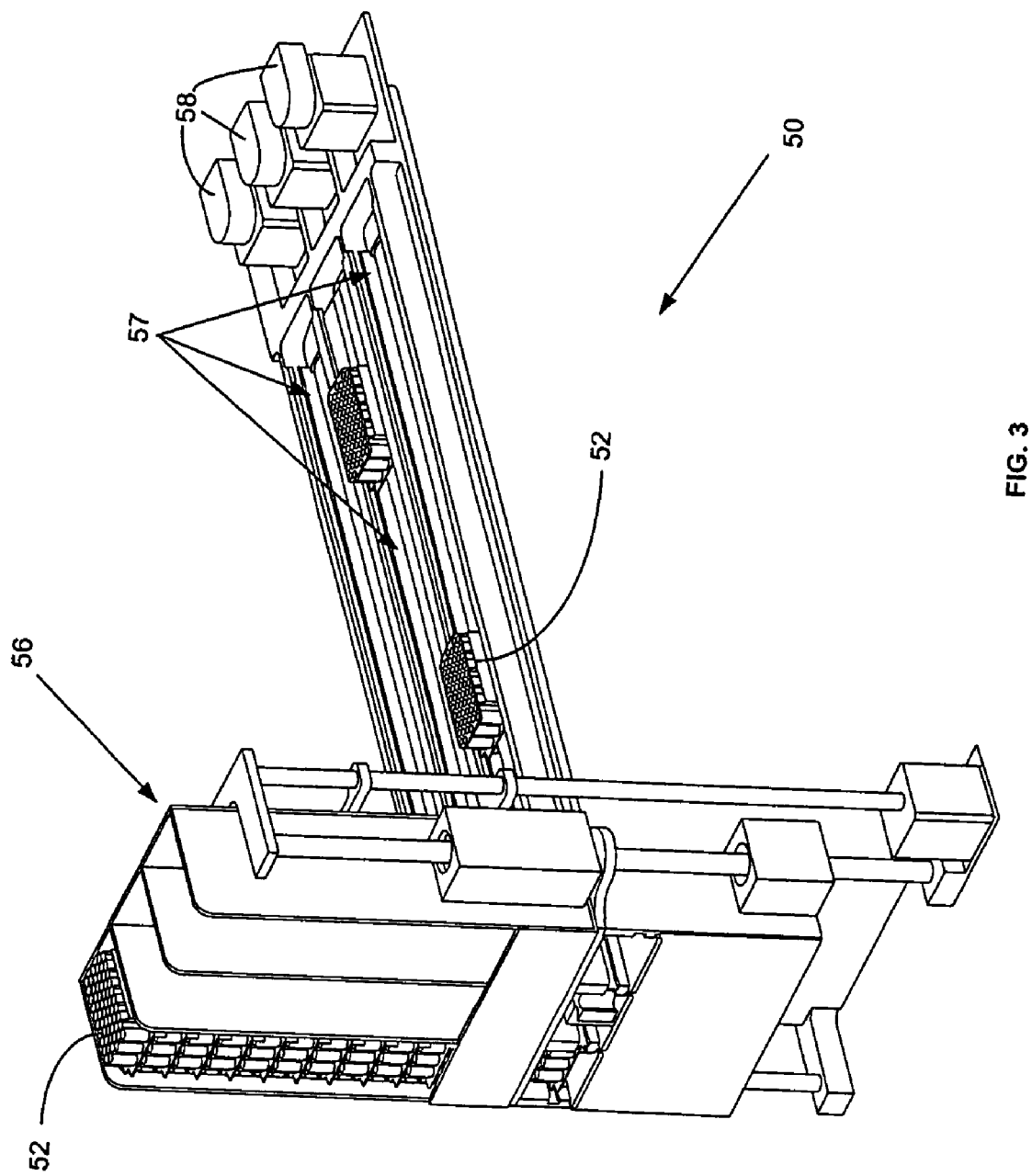
FIG. 3 is a perspective elevation view of an automated aliquot vessel array storage and handling unit that may be employed in the analyzer of FIG. 1.
Figure 4:
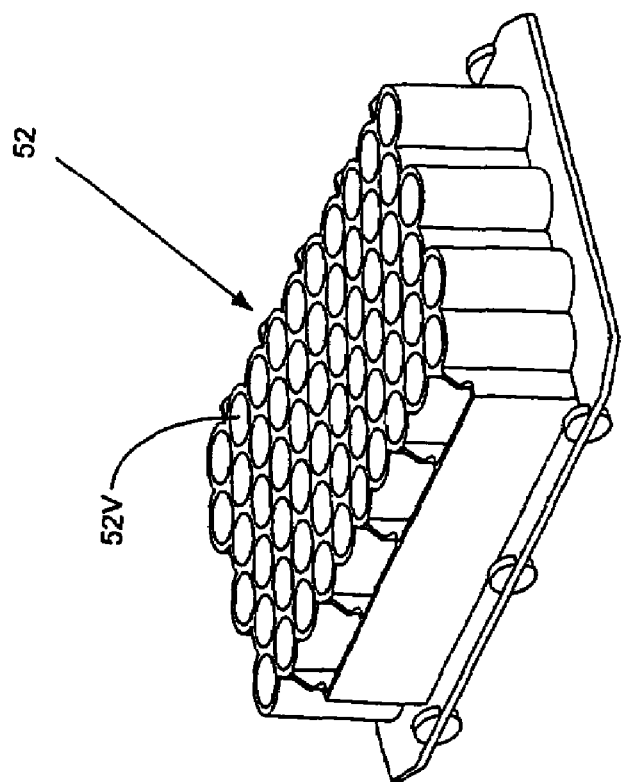
FIG. 4 is perspective elevation view of an aliquot vessel array that may be employed in the analyzer of FIG. 1.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels 52V in aliquot vessel array 52, as seen in FIG. 4, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and to then shuttle liquid probe 54P to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60 and 62 comprising a pair of conventional liquid reagent probes, 60P and 62P, respectively, are independently mounted and translatable between reagent storage areas 26 and 28, respectively. Probes 60P and 62P comprise conventional mechanisms for aspirating reagents required to conduct specified assays at a reagenting location from wells 32 in an appropriate reagent cartridge 30, the probes 60P and 62P subsequently being shuttled to a reagent dispensing location where reagent(s) are dispensed into reaction cuvettes 24. A number of reagent cartridges 30 are inventoried in controlled environmental conditions inside reagent storage areas 26 and 28; a key factor in maintaining high assay throughput is the ability to quickly and accurately shuttle reagent cartridges 30 inside reagent storage areas 26 and 28 to reagenting locations for access by probes 60P and 62P.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a sliding chute 65. In operation, used cuvettes 24 in which an assay has been finally conducted, are washed and dried in a wash station 67 of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like seen on load stations 61 and 63.

Figure 5:
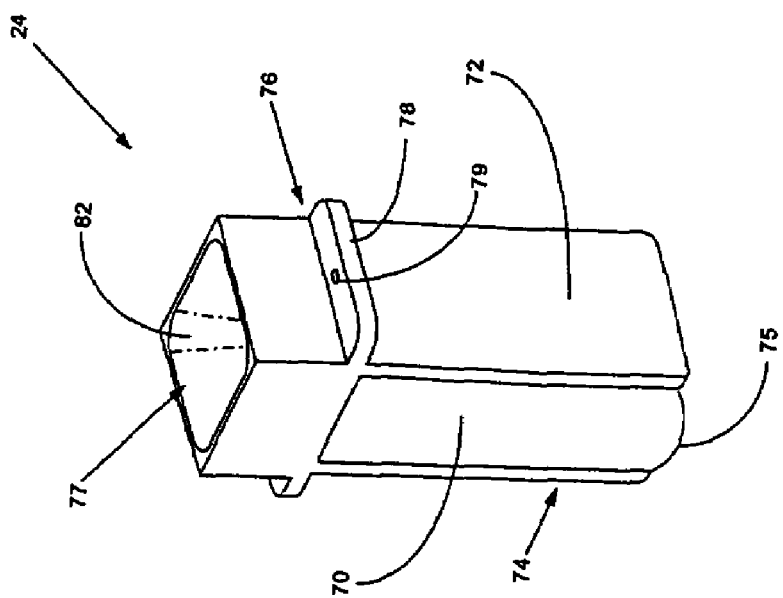
FIG. 5 is a perspective view of a typical reaction cuvette that may be employed in the analyzer of FIG. 1.
Figure 5A:
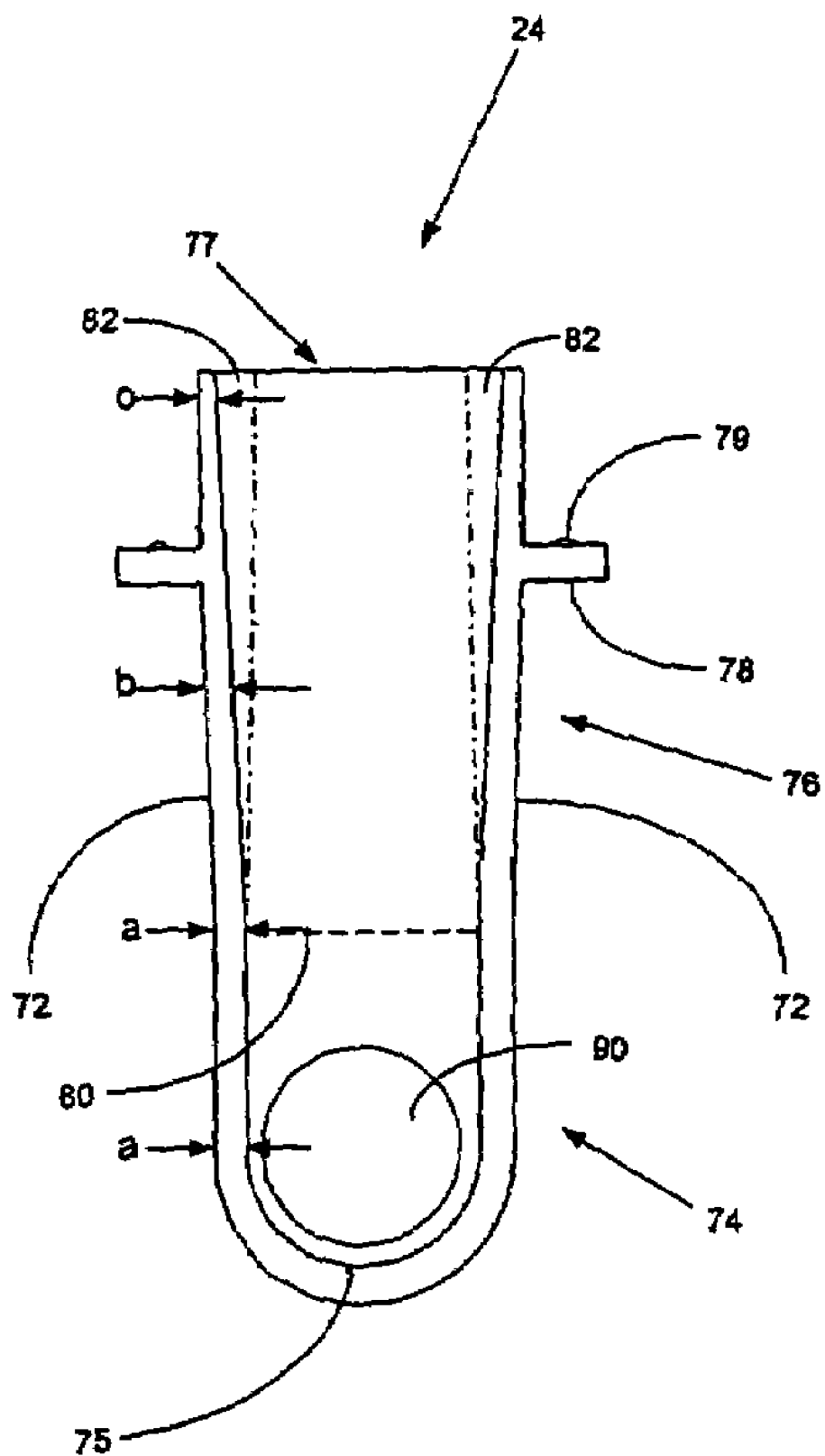
FIG. 5A is a section view showing the side walls of the reaction cuvette of FIG. 5.

FIG. 5 is an external isometric view of reaction cuvette 24, like that described in co-pending application Ser. No. 10/623.436 assigned to the assignee of the present invention, as having features to inhibit liquid wicking along an interior wall surface so that the presence of undesirable contaminants on the exterior surface of reaction cuvette 24 is minimized and the efficiency of washing by wash station 67 is increased. The reaction cuvette 24 shown in FIGS. 5 and 5A may be formed as an essentially rectangular box-shaped part 24 with a mutually opposed front wall and back wall 70 perpendicular to and separating two mutually opposed side walls 72. A generally rectangular lower section 74 closed by a curved bottom surface 75 supports an open top section 76 with opening 77. A pair of projecting ledges 78 are formed on opposing sides of cuvette 24, each having a latching bulge 79 to facilitate automated handling formed therein. As seen in FIG. 5A, the thickness "a" of side walls 72 is generally uniform within lower section 74 but gradually decreases between a junction, indicated by dashed line 80, between lower section 74 and the top section 76 and located generally about 40% of the distance from the bottom surface 75 to the top opening 77. Anti-wicking fillets 82 are formed as a smooth transition that effectively blends the intersections of front and back walls 70 and side walls 72. It may be seen in FIG. 5A that the wall thickness "a" of side walls 72 decreases smoothly to a value "b" about 75% of "a" and thereafter decreases smoothly to a value "c" about 60% of "a". Thus the internal dimensions of cuvette 24 slowly decrease from the value at opening 77 to the value at dashed line 80 to facilitate insertion of a drying boot seen in FIG. 10B and described later. Front and back walls 70 are similarly shaped for the same reason.

Figure 6:
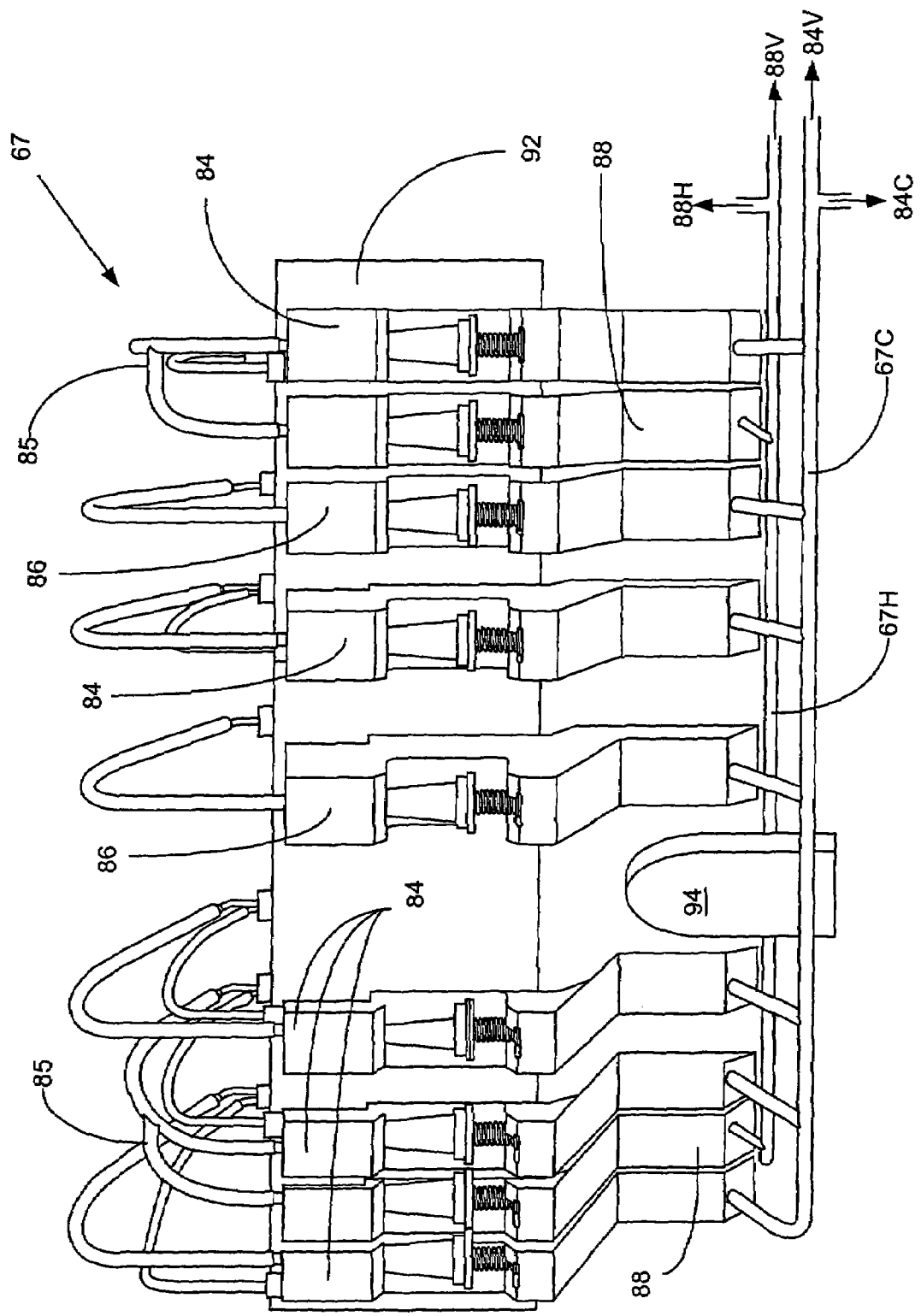
FIG. 6 is a front perspective view of the automated wash station of the present invention.
Figure 7:
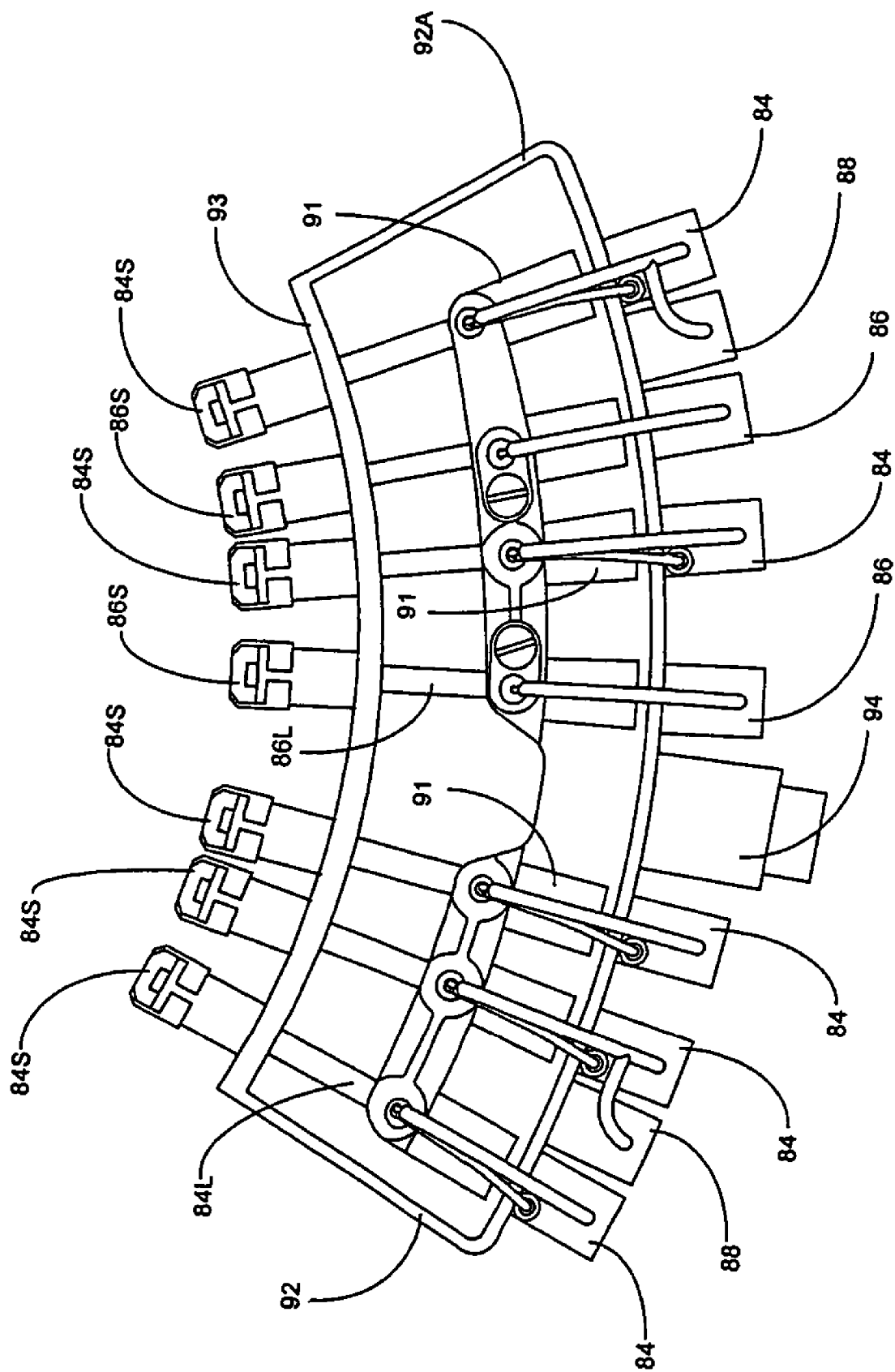
FIG. 7 is a top view of the automated wash station of FIG. 6.
Figure 8:
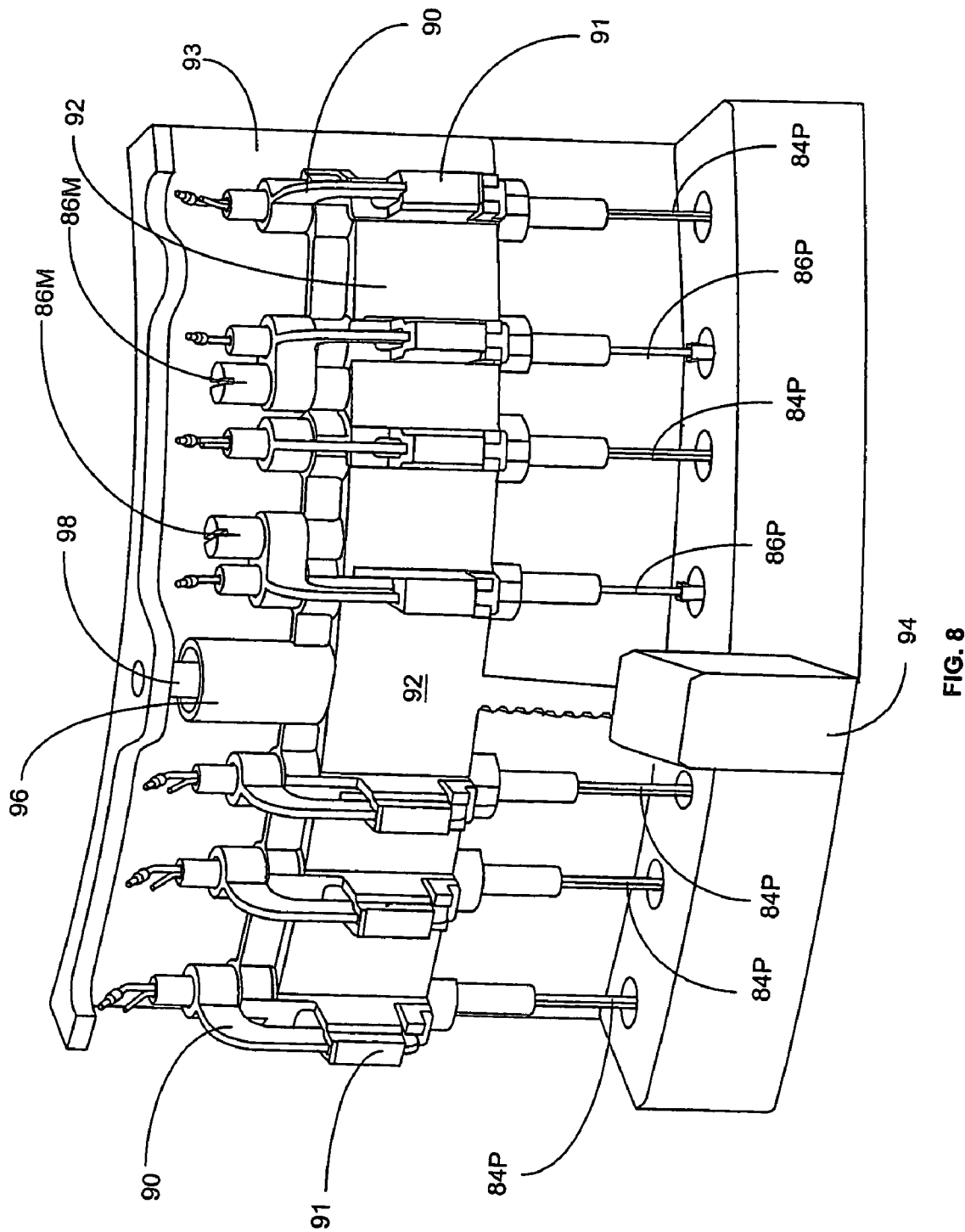
FIG. 8 is a front trimetric view of the automated wash station of the present invention with manifolds removed for purposes of clarity.
Figure 9:
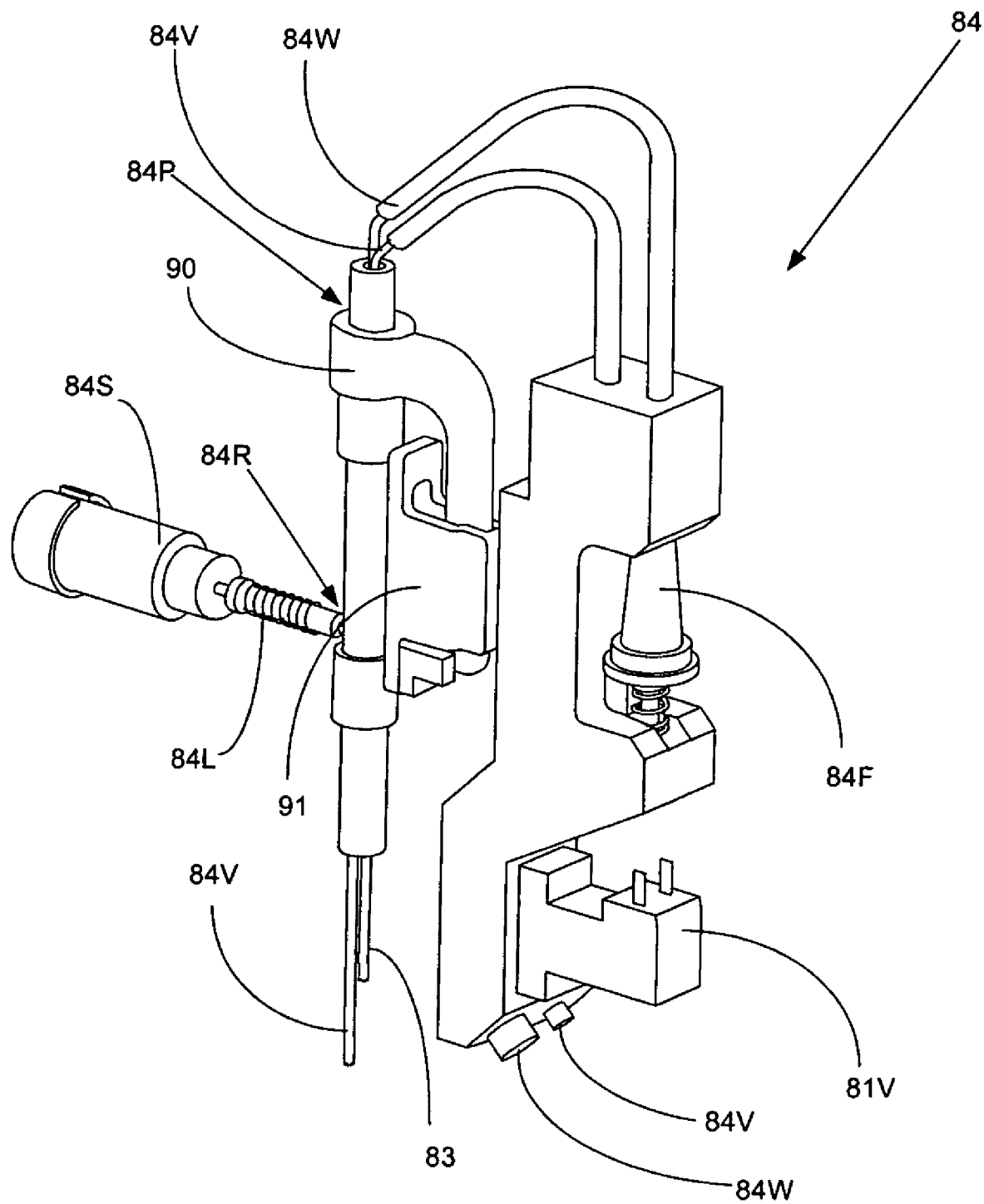
FIG. 9 is a perspective view of a washing probe useful in the wash station of FIG. 6.
Figure 10:
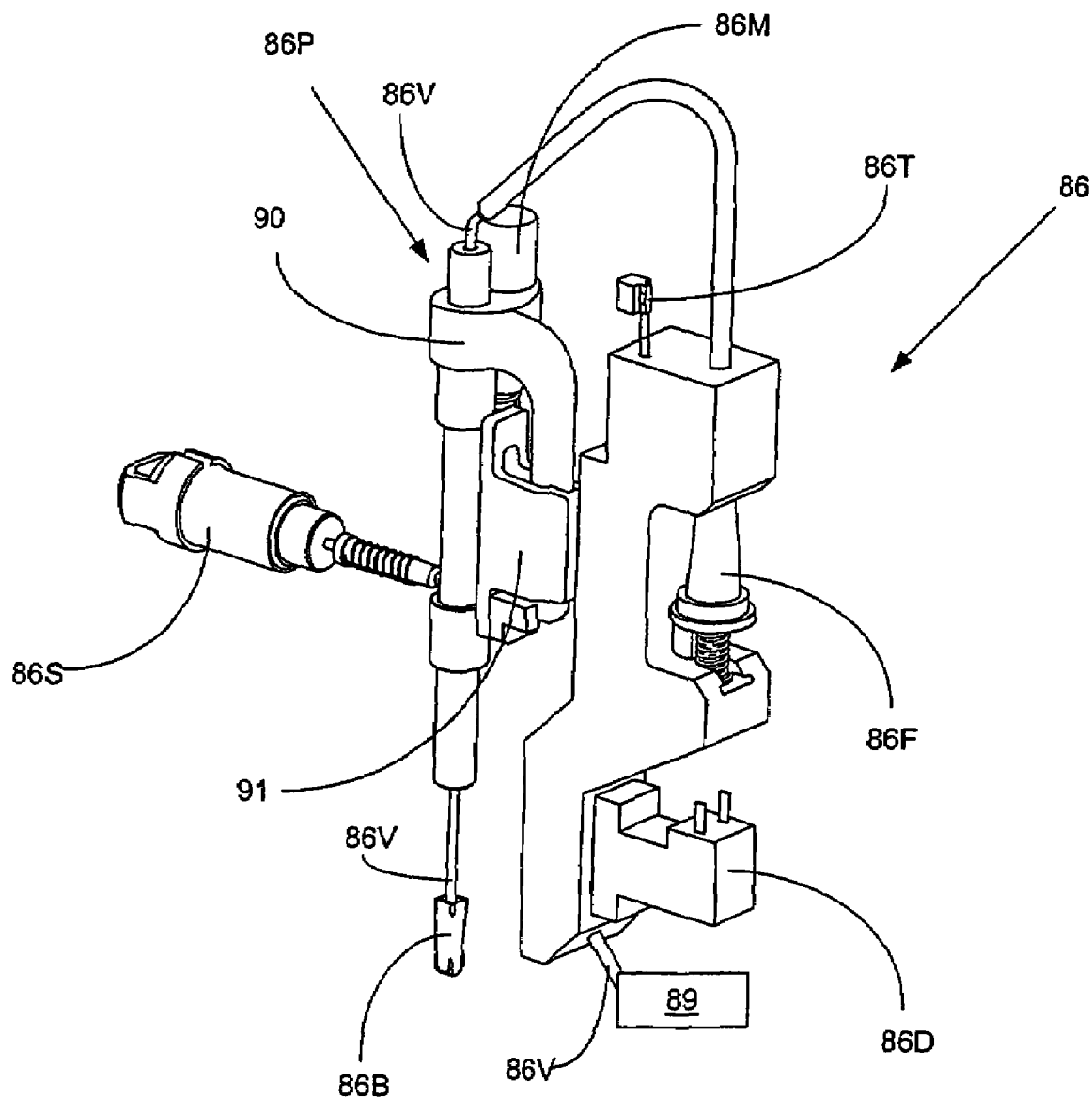
FIG. 10 is a perspective view of a drying probe useful in the wash station of FIG. 6.

Used cuvettes 24 are automatically cleaned by cuvette wash station 67 of the present invention, like seen in FIG. 6, wash station 67 comprising a number of washing manifolds 84, a number of drying manifolds 86, and a number of waste manifolds 88. Washing manifolds 84 and drying manifolds 86 are respectively in fluid communication with a corresponding number of washing probes 84P and drying probes 86P, best seen in FIG. 8, in which washing manifolds 84, drying manifolds 86 and waste manifolds 88 have been removed for purposes of clarity. FIG. 8 shows washing probes 84P and drying probes 86P as being vertically translatable by means of a curved vertical slide 92 comprising a collar 90 freely disposed inside a sleeve 91, sleeve 91 being mounted to curved slide 92, curved slide 92 attached to a stationary motor 94 and adapted to vertically translate a bearing portion 96 of curved slide 92 along a stationary post 98 (FIG. 8). A close inspection shows that motor 94 is adapted to vertically raise or lower curved slide 92 and thereby raise or lower washing probes 84P and drying probes 86P as long as the washing probes 84P and drying probes 86P are freely disposed inside sleeve 91. As seen in FIGS. 7, 9 and 10, each washing manifold 84 and drying manifold 86 is further associated with a washing probe solenoid 84S and a drying probe solenoid 86S, respectively, the washing manifolds 84 and a drying manifolds 86 being mounted to a curved plate 92A which is connected to stationary solenoid mounting rail 93.

Figure 10A:
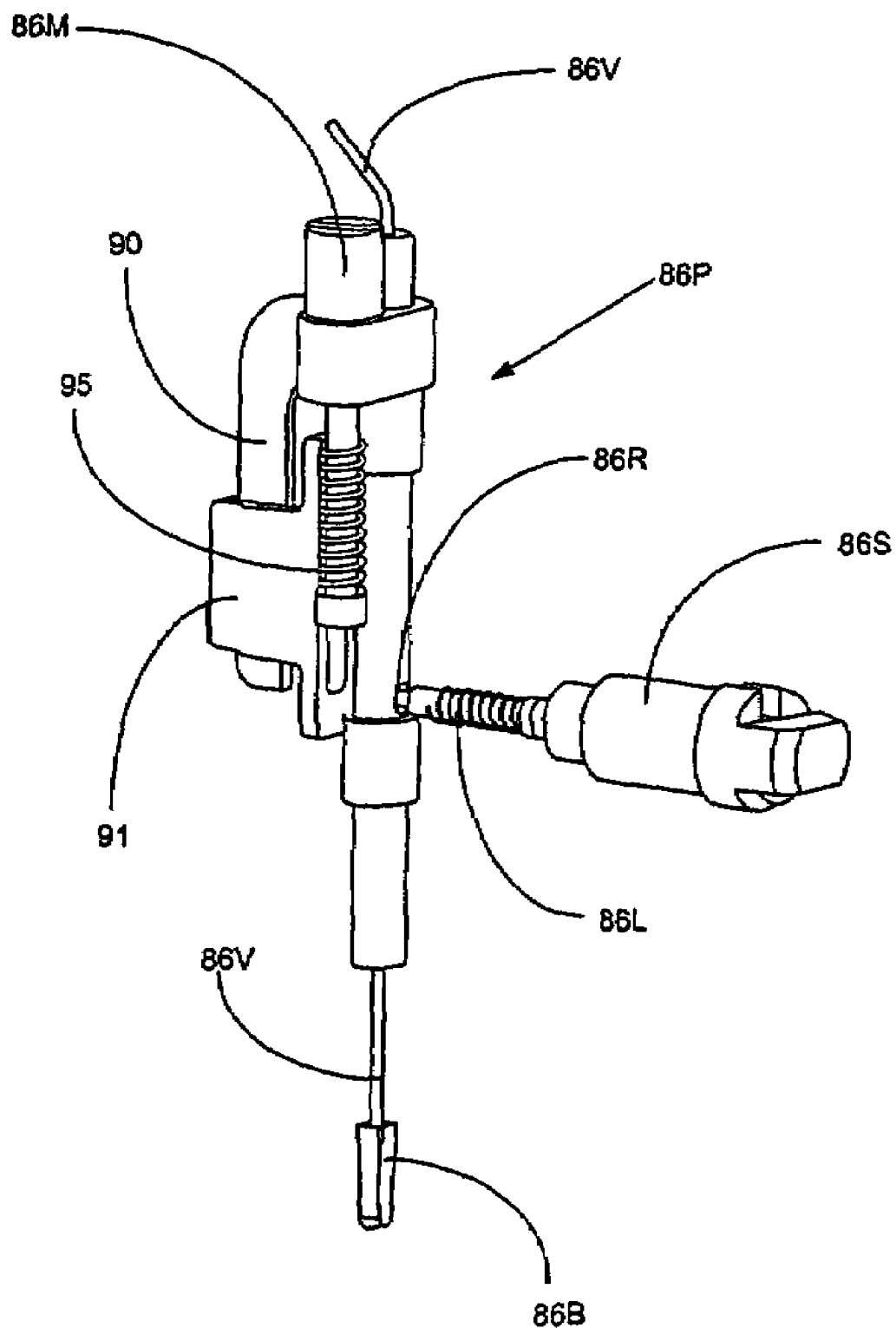
FIG. 10A is a perspective view of the drying probe of FIG. 10 engaged by a solenoid.

A key feature of the present invention is the independent selective activation of individual washing probe solenoids 84S and drying probe solenoids 86S to engage a locking portion 84L and 86L, respectively, into recesses 84R and 86R of individual washing probes 84P and drying probes 86P (FIGS. 9 and 10A) so as to selectively retain individual washing probes 84P and drying probes 86P in an upper non-operating position, solenoids 84S and 86S engaged, or to be freely lowered into an operating position when curved slide 92 is lowered by motor 94, solenoids 84S and 86S not engaged. FIG. 10A illustrates this feature in which a drying probe solenoid 86S is engaged into a recess 86R in the side of drying probe 86P; sleeve 91 is seen in a lowered position, however because of the engaged drying solenoid 86S, drying probe 86P has remained in its upper non-operating position and collar 90, although stationary, is vertically displaced "upwards" relative to sleeve 91. In FIG. 10A, curved slide 92 has been omitted for clarity but the reader will understand that due to sleeve 91 being attached to slide 92, the action of motor 94 raising and lowering slide 92 also raises and/or lowers drying probe 86P unless drying solenoid 86S is engaged into recess 86R. Washing probes 84P are similarly attached to slide 92, so that the action of motor 94 raising and lowering slide 92 also raises and/or lowers washing probes 84P unless washing solenoid 84S is engaged into recess 84R, as illustrated in FIG. 9.

Slide 92 is curved to match the radius of curvature of outer cuvette carousel 14 so that cuvette ports 20 holding reaction cuvettes 24 are located directly beneath washing probes 84P and drying probes 86P. Further, the radial distance between washing probes 84P and drying probes 86P matches a multiple of the radial distance between next adjacent cuvette ports 20 in order to create a mated array of washing probes 84P and drying probes 86P directly above cuvette ports 20. When curved slide 92 is positioned by motor 94 in its uppermost position, the lowermost portions of washing probes 84P and drying probes 86P are positioned above the top openings 77 of reaction cuvettes 24 in cuvette ports 20. Conversely, when curved rail 92 is lowered by motor 94 into its lowermost position and washing probe solenoids 84S and drying probe solenoids 86S are not engaged, washing probes 84P and drying probes 86P are freely lowered and positioned immediately above the bottom surface 75 of reaction cuvettes 24 in cuvette ports 20.

Figure 11:
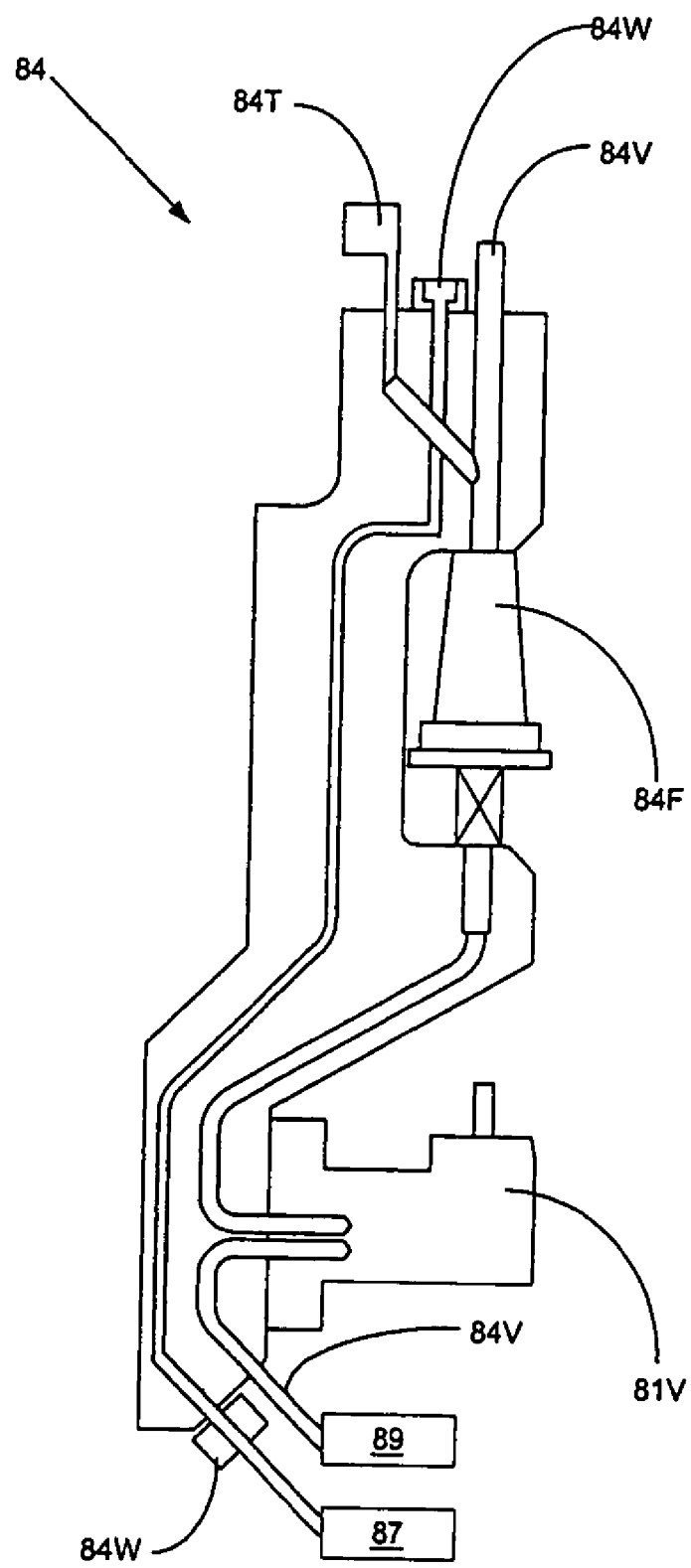
FIG. 11 is a section view of a washing manifold useful in the wash station of FIG. 6.

FIG. 9 further shows washing probe 84P as comprising a wash line 83 for supplying a pulsed stream of a cleaning detergent in de-ionized water or alternately a pulsed stream of rinsing de-ionized water from washing manifold 84, wash line 83 having a lowermost portion for extending into cuvettes 24 to be washed, an upper portion extending out of wash probe 84P into washing manifold 84 and exiting therefrom at a lowermost portion of washing manifold 84. In FIG. 11, washing manifold 84 may be seen to provide an uninterrupted pathway for wash tube 84W and an external connection to a source 87 of cleaning detergent in de-ionized water, and in the alternate, rinsing de-ionized water.

Washing probe 84P further comprises a vacuum line 84V also having a lowermost portion for extending into cuvettes 24 to be washed, an upper portion extending out of wash probe 84P into washing manifold 84 and exiting therefrom in a lowermost portion of washing manifold 84. In the instance of vacuum line 84V, as seen in FIG. 11, the pathway through washing manifold 84 includes an in-line filter 84F and an in-line relay valve 84D before exiting washing manifold 84 and being connected to a vacuum source 89. Relay valve 84D is operable to open or close vacuum line 84V so that vacuum source 89 may be directly connected to or disconnected from the lowermost portion of vacuum line 84V extending into cuvettes 24. A typical full washing operation on a cuvette 24 includes: (A1) a series of mini-washes described hereinafter using wash probe 84P for suction of reaction waste by vacuum line 84V into waste drain line 67C adapted to carry off biological and innocuous chemical wastes; (A2) delivering de-ionized or detergent water by wash tube 84W; and (A3) repeating the suction and delivering different numbers of times. After the last delivering, the water or detergent is left in the reaction cuvette 24; (B) a number of additional series of mini-washes with de-ionized water; and, (C) drying the reaction cuvette 24 with a drying probe 86P.

An important feature of washing station 67 as seen in FIGS. 6 and 7, is a connection of waste manifolds 88 to washing manifolds 84 by a hose 85 at a location between washing manifold 84 and wash probe 84P so that if desired, in particular in the instance that a reaction cuvette 24 to be washed has contained potentially harmful chemicals, the waste manifold 88 may be used in a first series of mini-washes to vacuum the potentially harmful waste from reaction cuvette 24 through the top portion of vacuum line 84V of wash probe 84P into hose 85, and into waste manifold 88. As seen in FIG. 12A, waste manifold 88 is essentially the same as a wash manifold 84, including filter 88F and relay valve 88D except that it provides a separate path for potentially harmful waste from hose 85 through tube 67H into a secure storage 88H. In this instance, the initial washing steps (A1-A3) above are conducted by waste manifolds 88 and the potentially harmful waste is discharged into secure storage 88H. In contrast, in the instance that an assay involves only biological and innocuous chemical waste and no potentially harmful agents, the initial washing steps (A1-A3) above are conducted only by washing manifolds 84 and vacuum line 84V deposits the biological and innocuous chemical reaction waste into a secure biological and innocuous chemical waste storage 84C.

Figure 12:
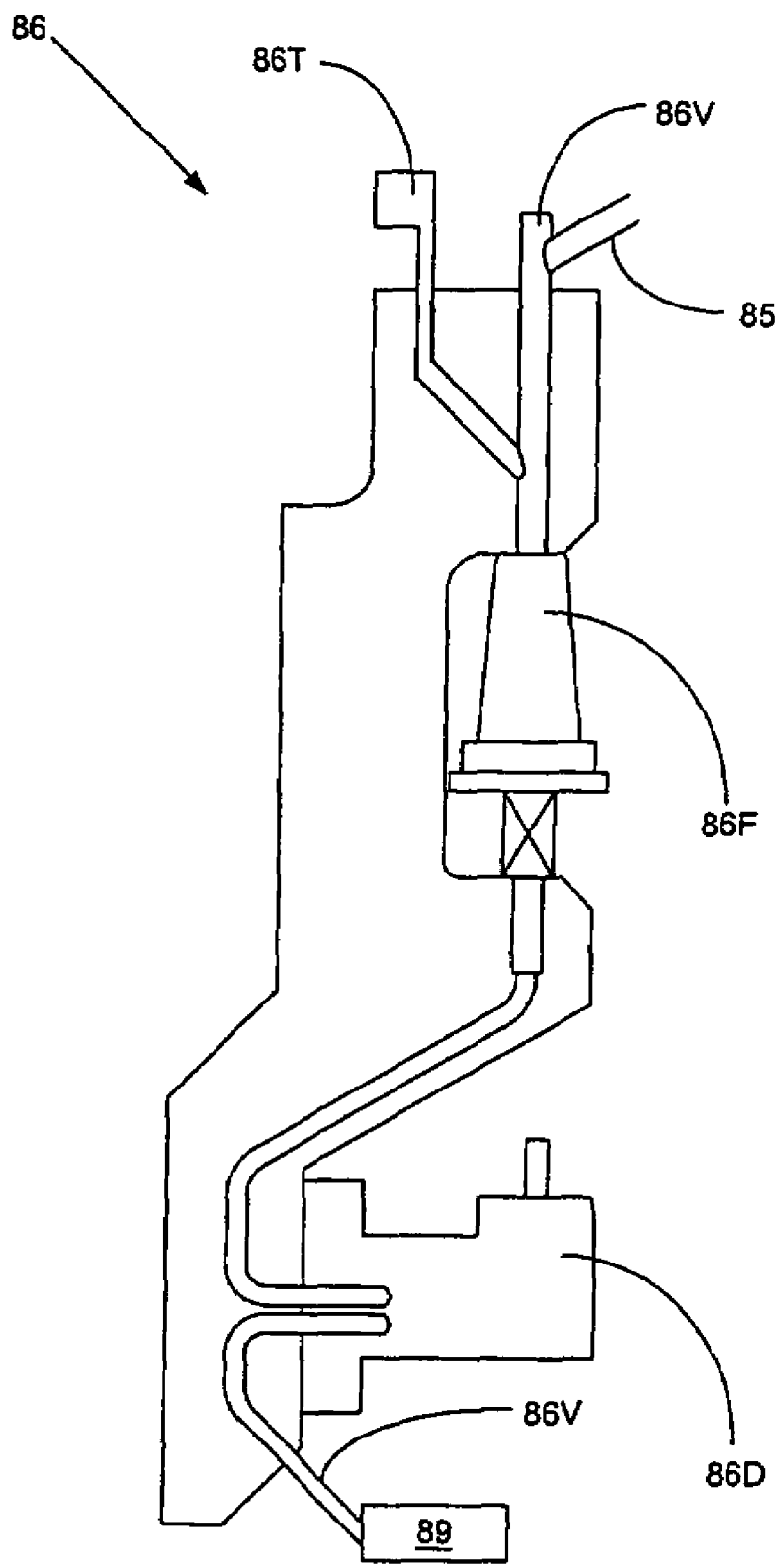
FIG. 12 is a section view of a drying manifold useful in the wash station of FIG. 6.
Figure 12A:
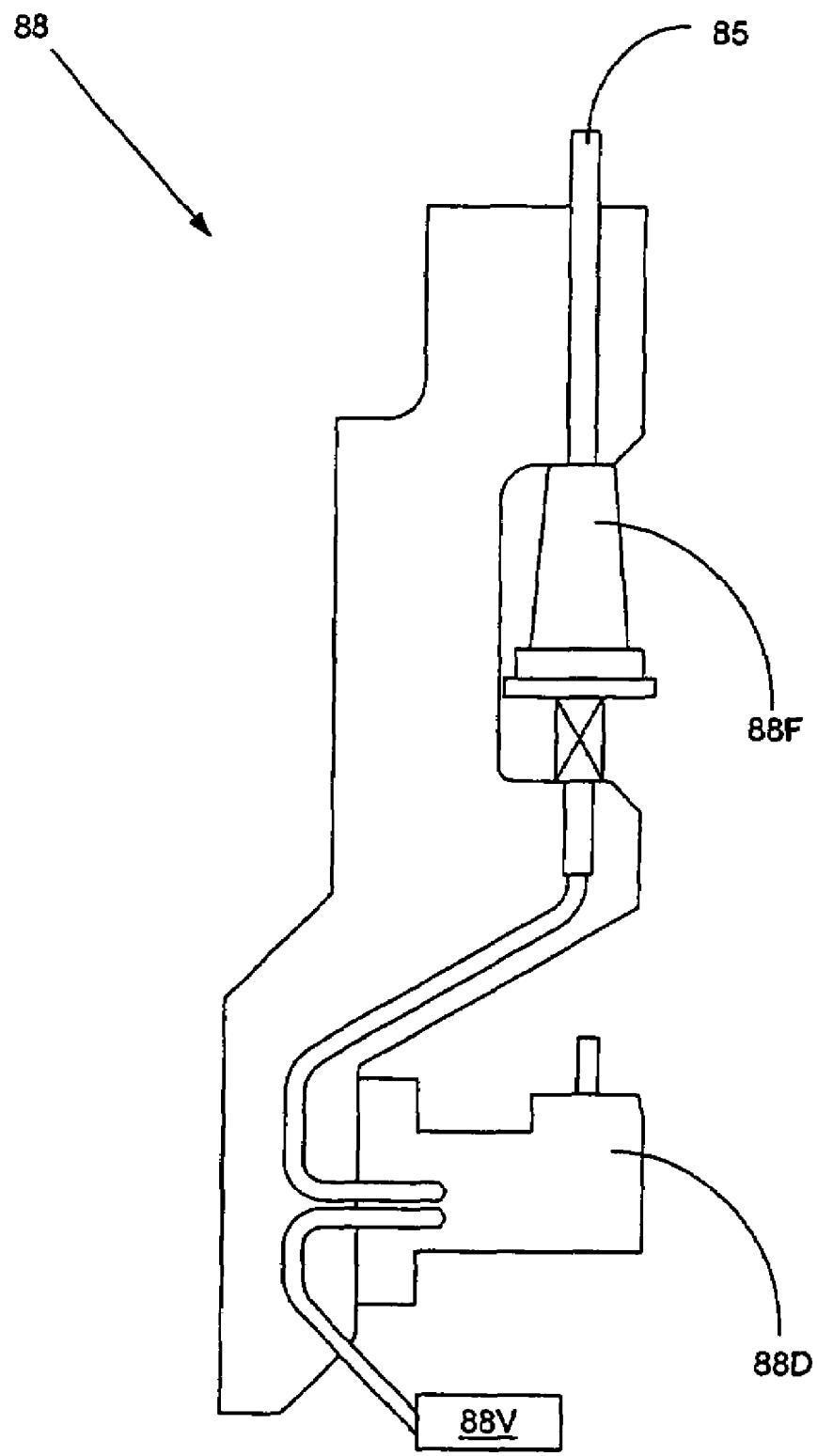
FIG. 12A is a section view of a waste manifold useful in the wash station of FIG. 6.

Drying manifold 86, seen in FIGS. 10 and 12, shows drying probe 86P as also comprising a vacuum line 86V having a lowermost portion for extending into cuvettes 24 to be dried, an upper portion extending out of drying probe 86P into drying manifold 86 and exiting in a lowermost portion thereof. In the instance of vacuum line 86V, as seen in FIG. 12, the pathway through drying manifold 86 includes an in-line filter 86F and an in-line relay valve 86D before exiting drying manifold 86 and being connected to vacuum source 89. Relay valve 86D is operable to open or close vacuum line 86V so that vacuum source 89 may be directly connected to or disconnected from the lowermost portion of vacuum tube 86V extending into cuvettes 24. Drying manifolds 86 and washing manifolds 84 optionally include a pressure transducer 86T or 84T respectively attached into vacuum line 86V or 84V respectively and adapted to measure vacuum pressure therein to detect, for example a partially clogged vacuum line.

Figure 10B:
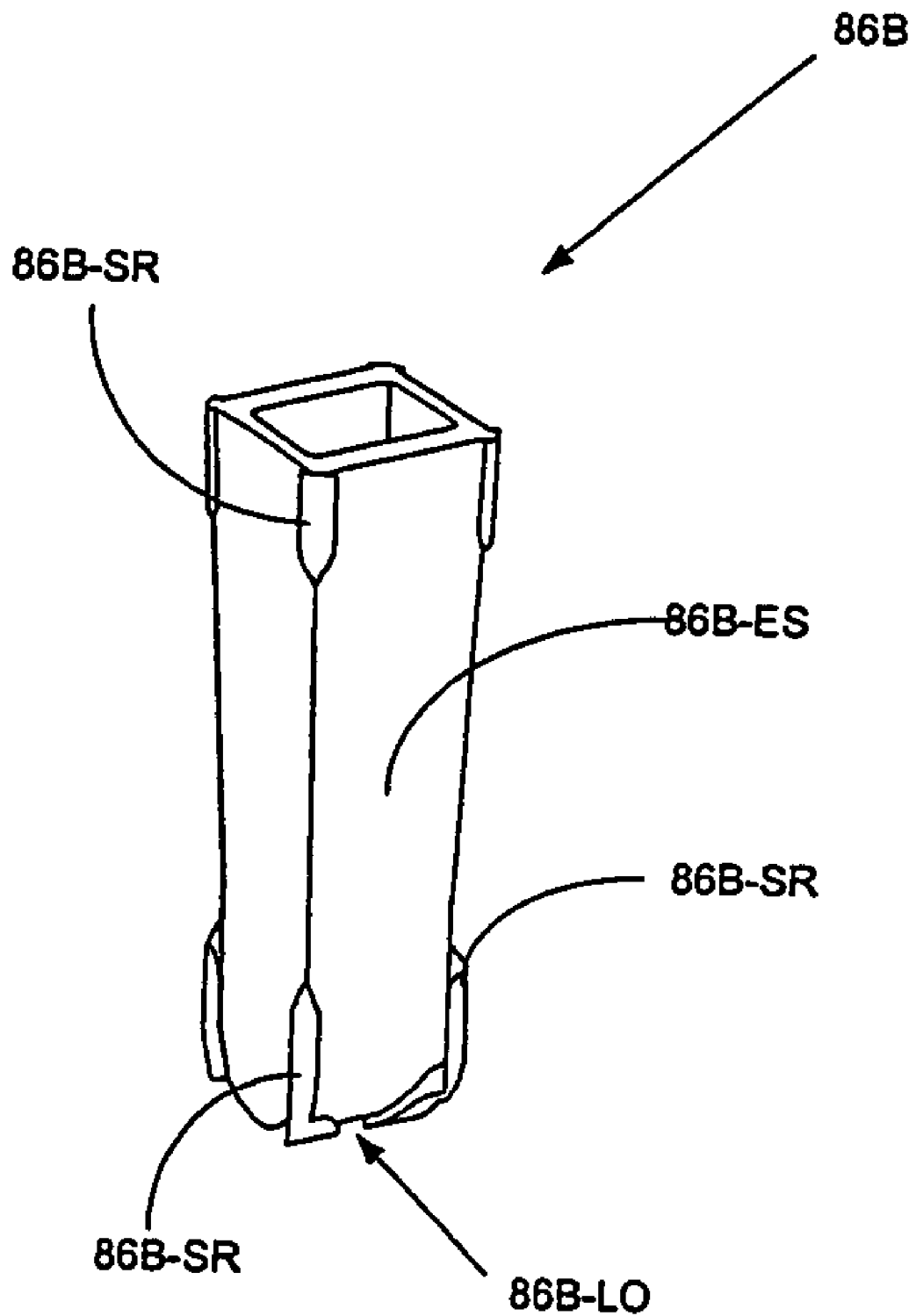
FIG. 10B is a perspective view of a drying boot useful in drying probe of FIG. 10.
Figure 13:
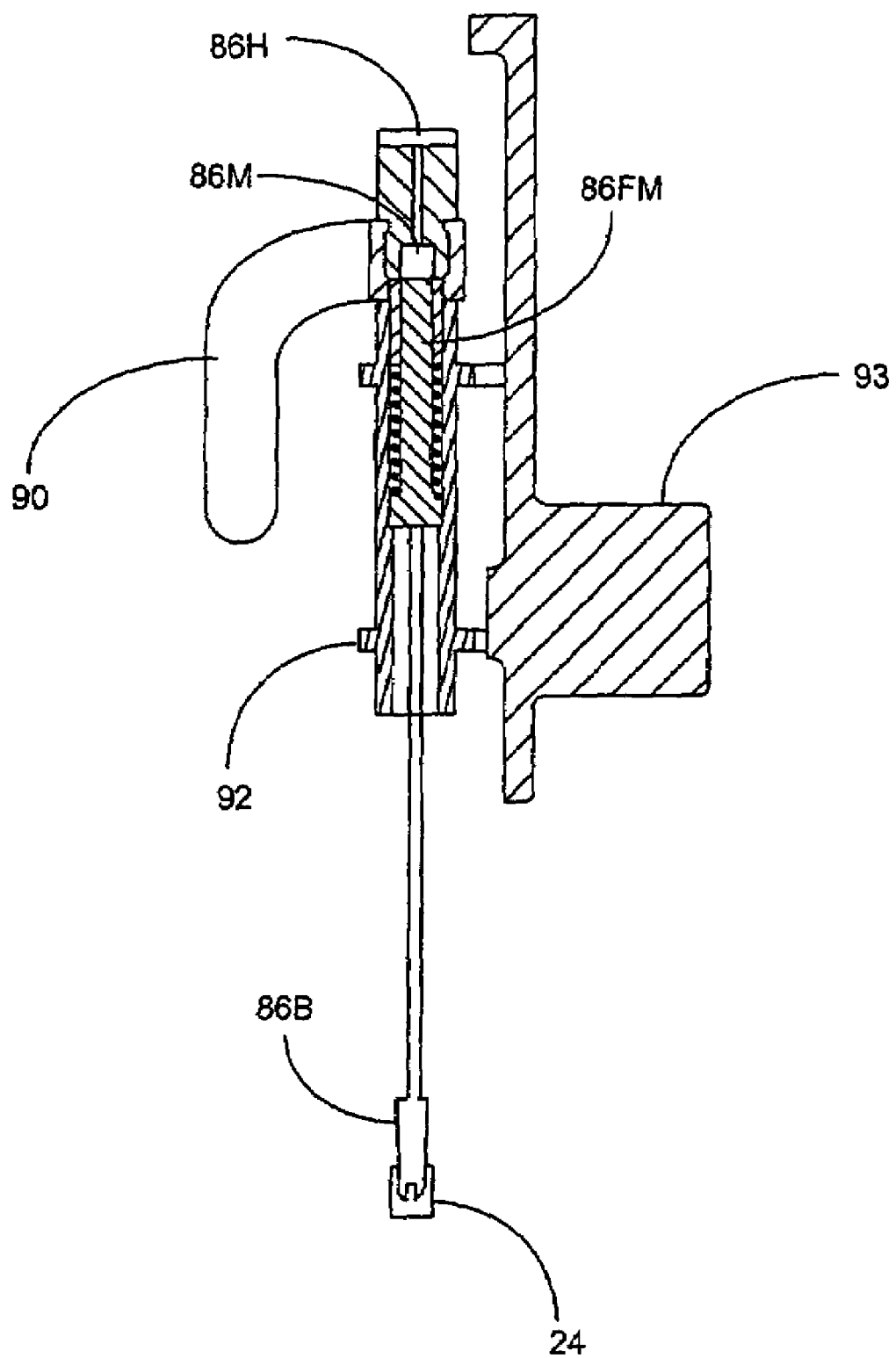
FIG. 13 is a section view of a break-away mechanism useful in the wash station of FIG. 6; and, FIG. 14 is a top view of a particular embodiment of the wash station of FIG. 6.

The lowermost portion of drying probe 86P concludes with a drying boot 86B, FIG. 10B, having side ridges 86B-SR and lateral openings 86B-LO on its external surfaces 86B-ES that act to generate a knife-like flow of drying air from outside drying probe 86 around boot 86B whenever 86D is opened to connect vacuum tube 86V of drying probe 86 to vacuum source 98 and boot 86B is inserted within a cuvette 24. Vacuum source 98 and relay valve 86D are operational before the drying probe 86P is lowered into cuvette 24 and is de-activated a few seconds after the drying probe 86P is removed from cuvette 24. Once boot 86B touches the bottom of a cuvette 24, drying probe 86P is optionally raised slightly upwards and then downwards to the bottom again in order to dislodge water trapped inside cuvette 24. The side features of drying boot 86B are purposefully dimensioned so that drying boot 86B fits into a cuvette 24 with a very small clearance or slight interference fit in order to maximize the effectiveness of such a drying-knife effect. Due to such a close fit, there may exist resistance to the lowering of drying probe 86P that must be overcome in order for boot 86B to be inserted fully into a cuvette 24. In order to overcome this resistance, drying probe 86P further includes a "break-away" magnet comprising a magnet portion 86M within collar 90 and a ferromagnetic portion 86FM within slide 92. Best seen in FIGS. 10A and 13, a spring 95 biases collar 90 against slide 92 so that whenever solenoid 86S is not engaged into drying probe 86 and slide 92 is lowered by motor 94, drying probe 86 is lowered into a cuvette 24 to be dried with an additional spring-loaded force up to the magnetic break-away force between the magnet portion 86M and the ferromagnetic portion 86FM. In contrast, whenever a solenoid 86S is engaged into a drying probe 86 so that the drying probe 86 is not to be lowered when slide 92 is lowered by motor 94, the magnetic forces between magnet portion 86M and ferromagnetic portion 86FM are overcome, magnet portion 86M and ferromagnetic portion 86FM automatically separate.

From the description provided above, key features of the present invention include: (a) the ability to independently selectively lower a wash probe 84P or a drying probe 86P into a reaction cuvette 24 in cuvette ports 20 as outer cuvette carousel 14 is rotated step-wise; (b) the ability to provide additional spring-biased force to drying probes 86P being lowered into reaction cuvettes 24 to be dried so that boot 86B is fully inserted thereinto; (c) the ability to selectively activate waste manifolds 88 connected to washing manifolds 84 so that a washing manifold is effectively by-passed and potentially harmful waste from assays may be segregated from biological and innocuous chemical reaction waste; and (d) a drying boot 86B having side ridges 86B-SR and lateral openings 86B-LO on its external surfaces that act to generate a knife-like flow of drying air. For reasons of reducing the cost-per-reportable result of an assay, it is advantageous that used reaction cuvettes 24 be washed in cuvette wash station 67 and reused in subsequent reaction assays. For reasons of increasing assay throughput within analyzer 10, it is desirable to expend minimum time and resources in sufficiently washing reaction cuvettes 24. It has been learned, however, that not all vestiges of all assay reaction residues can be cleanly removed in one or two washing operation, and that assay reaction residues can only be removed to less than 1 part-per-million remaining in a cuvette 24 by subjecting the cuvette 24 to four cleansing operations, (3 series of mini-washes, steps 1, 2 and 3 in Table 1 below, followed by drying). Furthermore, it has been discovered that assay reaction residues can be reduced to less than 10 part-per-million in a cuvette with three cleansing operations, (2 series of mini-washes, steps 4 and 5 in Table 1 below, followed by drying). A key advantage of the present invention is the ability to clean a used reaction cuvette in analyzer 10 so that whenever an assay in a first group of assays is scheduled to be next performed in a used but cleaned reaction cuvette, the used reaction cuvette is automatically subjected to an additional cleaning operation. This advantage is achieved by operating washing station 67 to selectively clean certain used reaction cuvettes 24 with four cleansing operations, at the same time that whenever an assay in a second group of assays is scheduled to be next performed in a reaction cuvette 24, that reaction cuvette 24 is selectively cleaned with only three cleansing operations, these series of mini-washes comprising injection of approximate volumes of wash or rinse water in the instance that reaction cuvette 24 can contain about 500 uL liquid as shown in Table 1 for the cleansing operations described in Table 2. It should be noted that these washing operations are essentially dilution operations in which an initial comparatively small volume of water (relative to the fluid capacity of the cuvette 24) is injected into a used reaction cuvette 24 in order to initially remove the sediment at the bottom of a reaction cuvette 24. Subsequently, comparatively larger volumes of water (relative to the initial volume of water) are injected into the cuvette 24 in order to remove the more diluted waste remaining therein. In practicing the present invention, the full menu of assays analyzer 10 is equipped to perform is divided into two groups: a first group of assays previously determined to potentially have inaccurate assay results if assay reaction residues in a cleansed cuvette 24 are greater than 1 part-per-million, and a second group of assays previously determined to not potentially have inaccurate assay results if assay reaction residues in a cleansed cuvette 24 are greater than 10 part-per-million.

TABLE 1

| Step | 1st Wash Volume ± 25 | 2nd Wash Volume ± 25 | 3rd Wash Volume ± 25 | Fill Volume ± 25 | Total Volume ± 25 |
| --- | --- | --- | --- | --- | --- |
| 1 | 100 uL | 200 uL | 200 uL | 260 uL | 760 uL |
| 2 | 100 uL | 390 uL |  | 420 uL | 910 uL |
| 3 | 100 uL | 420 uL |  | 420 uL | 940 uL |
| 4 | 100 uL | 150 uL | 200 uL | 390 uL | 740 uL |
| 5 | 100 uL | 420 uL |  | 420 uL | 940 uL |

In its broadest sense, the term cleansing operation includes any of washing or rinsing or drying. This independent selective cleaning of cuvettes 24 depending upon what assay is scheduled to be next performed therein increases the overall throughput of analyzer 10 since the cuvettes 24 that have been sufficiently cleaned after only three cleansing operations are immediately available to be reused in a subsequent assay.

Figure 14:
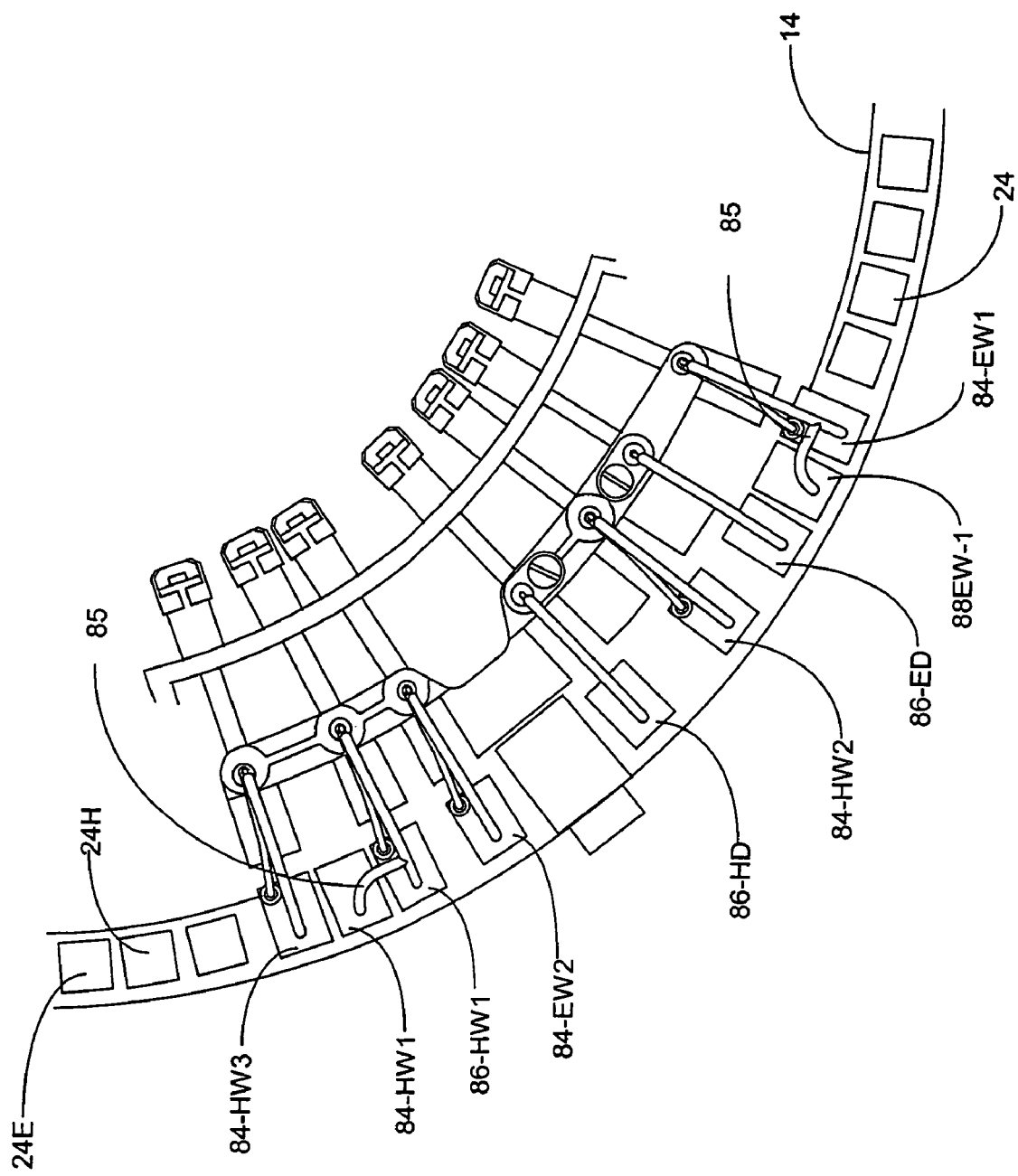

The present invention can be illustrated in a non-limiting embodiment in which reaction carousel 12 has cuvette ports 20 is rotated in a clock-wise direction using stepwise 1.5 second movements separated by a 2.1 second dwell time during which dwell time, wash station 67 may or may not perform washing, rinsing or drying operations on a cuvette 24 stopped beneath washing probes 84 or drying probes 86. For purposes of this illustration, reaction carousel 12 is dimensioned so as to have 184 cuvettes 24 located in cuvette ports 20 in outer cuvette carousel 14. Each 5 or 7 clock-wise stepwise rotations of 77 cuvette locations by reaction carousel 12 transports a cuvette 24 to another location relative to its original location but within the operation zone of wash station 67. Features similar to these are known to improve operational simplicity of analyzer 10 but are not necessary to perform the present invention. The above different washing and drying operations for the first and second group of assays in cuvettes 24 are illustrated in the partial view of analyzer 10 seen in simplified FIG. 14 in which the different washing probes 84 and drying probes 86 are identified according to which washing and drying operations are performed thereby. In particular, as seen in Table 2, the components in FIG. 14 may be operated to achieve cleaning as described herein.

TABLE 2

| Component | Description |
| --- | --- |
| Cuvette 24E | A cuvette in outer cuvette carousel 14 in which an assay in the second group of assays is scheduled to be next performed. |
| Washing probe 84-EW1 | A probe in which a first washing operation with a series of mini-washes using a total of 740 uL rinse water is conducted on a cuvette 24 in which an assay in the second group of assays is scheduled to be next performed. |
| Washing probe 84-EW2 | A probe in which a second washing operation with a series of mini-washes using a total of 940 uL rinse water is conducted on a cuvette 24 in which an assay in the second group of assays is scheduled to be next performed. |
| Drying probe 86-ED | A probe in which a drying operation is conducted on a cuvette 24 in which an assay in the second group of assays is scheduled to be next performed. |
| Cuvette 24H | A cuvette in which an assay in the first group of assays is scheduled to be next performed. |
| Washing probe 84-HW1 | A probe in which a first washing operation with a series of mini-washes using a total of 760 uL rinse water washing solution is conducted on a cuvette 24 in which an assay in the first group of assays is scheduled to be next performed. |
| Washing probe 84-HW2 | A probe in which a second washing operation with a series of mini-washes using a total of 910 uL rinse water is conducted on a cuvette 24 in which an assay in the first group of assays is scheduled to be next performed. |
| Washing probe 84-HW3 | A probe in which a third washing operation with a series of mini-washes using a total of 940 uL rinse water is conducted on a cuvette 24 in which an assay in the first group of assays is scheduled to be next performed. |
| Drying probe 86-HD | A probe in which a drying operation is conducted on a cuvette 24 in which an assay in the first group of assays is scheduled to be next performed.. |

With the parameters provided for this exemplary embodiment of analyzer 10, computer 15 operates wash station 67 in coordination with the operation of reaction carousel 12 so that cuvette 24H is subjected to an additional rinsing operation in order to ensure its readiness for a subsequent assay in the first group of assays. Clearly, the additional cleaning operation could comprise any of washing or rinsing or drying operations.

For the purpose of first illustrating cleaning of a cuvette 24E in which assay in the second group of assays is scheduled to be next performed, after sample has been added to a cuvette 24E by probe 54P of sample aspiration and dispense arm 54 and appropriated reagents added to cuvette 24E by probe 60P of reagent arm 60 for example to perform a biological or chemical assay, reaction carousel 12 rotates until the chemical assay in cuvette 24E is completed. As defined above, cuvette 24E will be moved beneath washing probe 84-EW1 where a first washing operation is to be conducted. Washing station 67 is operated such that each time reaction carousel 12 is stopped for a dwell-time between step-wise rotations, curved slide 92 is lowered by motor 94 into its lowermost position and solenoids 84S and 86S are activated or engaged into washing probes 84 and drying probes 86 if it is desired that the washing probes 84 and drying probes 86 not be lowered into cuvettes 24 below. Thus, only the solenoid 84S associated with washing probe 84-EW1 would remain unactivated or disengaged so that the action of motor 94 lowering slide 92 also lowers only washing probe 84-EW1. The reader will appreciate that when analyzer is in normal operation, a cuvette 24 is located beneath each of the washing probes 84 and drying probes 86 so that it is necessary that the only solenoid 84S or 86S to be disengaged from its respective washing probe 84 or drying probe 86 is the solenoid(s) 84S associated with the washing probe(s) 84 or drying probe(s) 86 to be activated during each dwell-time of carousel 12.

During a first dwell time, cuvette 24E is subjected to a series of washing operation in which chemical reaction waste is aspirated by vacuum line 84V into biological and chemical waste storage 84C, de-ionized rinse water is injected into cuvette 24E by wash tube 84W, rinse water is aspirated from cuvette 24E by vacuum line 84V, the rinsing operation is repeated twice, and finally cuvette 24E is filled with water by wash tube 84W. As described previously, however, if the chemical assay performed in cuvette 24E involved potentially harmful chemicals, the potentially harmful reaction waste would be aspirated instead by vacuum line 88V into secure storage 88H. Subsequent to this first washing operation by washing probe 84-EW1, cuvette 24E is transported by 5 step-wise rotations of reaction carousel 12 to washing probe 84-EW2 where de-ionized rinse water is injected into cuvette 24E by wash tube 84W, rinse water is aspirated from cuvette 24E by vacuum line 84V, the rinsing operation is repeated, and finally cuvette 24E is filled with water by wash tube 84W, all during the dwell time. Subsequent to this second washing operation, cuvette 24E is transported by 7 step-wise rotations of reaction carousel 12 to drying probe 86-ED where rinse water is aspirated from cuvette 24E by vacuum line 86V. As described before, solenoids 84S and 86S are un-engaged or engaged into washing probes 84 and drying probes 86 as appropriate during these selectively independent operations.

The cleaning of a cuvette 24H in which an which assay in the first group of assays is scheduled to be next performed may be similarly described as follows: after sample has been added to a cuvette 24H by probe 54P of sample aspiration and dispense arm 54 and appropriated reagents added to cuvette 24E by probes 61P and 62P of reagent arms 61 and 62, respectively, for example to perform a biological assay, reaction carousel 12 rotates until the assay in cuvette 24H is completed. As defined above, cuvette 24H will be at washing probe 84-HW1 where a first washing operation is conducted in which cuvette 24H is subjected to a series of washing operation in which potentially harmful reaction waste is aspirated by vacuum line 88V into secure waste storage 88H, diluted detergent water is injected into cuvette 24H by wash tube 84W, detergent water is aspirated from cuvette 24H by vacuum line 88V, the rinsing operation is repeated twice, and finally cuvette 24H is filled with diluted detergent water by wash tube 84W. After 7 step-wise rotations of cuvette carousel 12, cuvette 24H is subjected to a second washing operation by washing probe 84-HW2, and after 5 additional step-wise rotations of cuvette carousel 12, cuvette 24H is subjected to a third washing operation by washing probe 84-HW3. Subsequent to this third washing operation, cuvette 24H is transported by 7 step-wise rotations of reaction carousel 12 to drying probe 86-ED where rinse water is aspirated from cuvette 24E by vacuum line 86V.

The details of performing the operations described within an automated clinical analyzer system is a task regularly encountered within the art and need not be described herein. It is sufficient that the teachings of the present invention, that used reaction cuvettes may be selectively cleansed depending upon the identity of the assay scheduled to be next performed therein. In an obvious alternate embodiment of the present invention, wash station 67 may be operated as described above so that a used reaction cuvette 24 in analyzer 10 is automatically subjected to an additional cleaning operation depending upon the identity of the assay performed therein. This objective of selective cleaning is partially achieved by providing a number of washing and drying manifolds, each of which is independently selectively activated to perform or not perform a cleaning operation, depending upon the identity of either the assay to be next performed therein or the identity of the assay perviously performed therein. For these reasons, the present invention is not limited to those embodiments precisely shown and described in the specification but only by the following claims.

We claim:

1. A method for cleansing a used reaction cuvette such that whenever an assay in a first group of assays is determined to be scheduled to be next performed in the cuvette by examining an identity of assays yet to be performed, the cuvette is cleansed by a first series of cleansing operations and whenever an assay in a second group of assays is determined to be scheduled to be next performed in the cuvette by examining the identify of assays yet to be performed, the cuvette is cleansed by a second different series of cleansing operations.

2. The method of claim 1 wherein the first group of assays comprises assays previously determined to potentially have inaccurate assay results if reaction residues in a cleansed used cuvette are greater than a known value and wherein the second group of assays comprises assays previously determined to not potentially have inaccurate assay results if reaction residues in a cleansed used cuvette are greater than the known value.

3. The method of claim 1 wherein the cleansing operations comprise a series of mini-washes followed by vacuum drying the cuvette.

4. The method of claim 1 wherein the first series of cleansing operations includes more cleansing operations than the second series of cleansing operations.

5. The method of claim 3 wherein the assays involve potentially harmful agents and residue from the mini-washes is discharged into a first secure storage and wherein the assays involve biological or innocuous chemical agents and residue from the mini-washes is discharged into a second secure storage.

* * * * *